(12) United States Patent
Sato et al.

(10) Patent No.: US 7,718,701 B2
(45) Date of Patent: May 18, 2010

(54) ANTIPRURITIC AGENT

(75) Inventors: Fumie Sato, Kanagawa (JP); Iwao Arai, Tokyo (JP); Norikazu Takano, Tokyo (JP); Tohru Tanami, Tokyo (JP); Makoto Yagi, Tokyo (JP)

(73) Assignees: Taisho Pharmaceutical Co., Ltd., Tokyo (JP); Fumi Sato, Kanagawa (JP)

( * ) Notice: Subject to any disclaimer, the term of this patent is extended or adjusted under 35 U.S.C. 154(b) by 1437 days.

(21) Appl. No.: 10/493,693

(22) PCT Filed: Aug. 7, 2003

(86) PCT No.: PCT/JP03/10051

§ 371 (c)(1),
(2), (4) Date: Apr. 27, 2004

(87) PCT Pub. No.: WO2004/014394

PCT Pub. Date: Feb. 19, 2004

(65) Prior Publication Data

US 2005/0009917 A1  Jan. 13, 2005

(30) Foreign Application Priority Data

Aug. 9, 2002 (JP) ............................. 2002-234011

(51) Int. Cl.
A01N 53/00 (2006.01)
C07C 59/00 (2006.01)
C07C 69/74 (2006.01)

(52) U.S. Cl. ....................... 514/573; 514/887; 514/861; 554/214; 560/121; 560/122

(58) Field of Classification Search ................. 514/573, 514/887, 861; 554/214; 560/122, 121
See application file for complete search history.

(56) References Cited

U.S. PATENT DOCUMENTS

| 4,454,339 | A |   | 6/1984  | Skuballa et al. |
|-----------|---|---|---------|-----------------|
| 4,699,920 | A |   | 10/1987 | Skuballa et al. |
| 4,789,685 | A |   | 12/1988 | Skuballa et al. |
| 4,870,104 | A |   | 9/1989  | Vorbruggen et al. |
| 4,983,629 | A |   | 1/1991  | Vorbruggen et al. |
| 5,491,254 | A | * | 2/1996  | Sato et al. ................... 560/121 |
| 5,545,666 | A | * | 8/1996  | Sato et al. ................... 514/530 |
| 5,591,446 | A |   | 1/1997  | Melnik et al. |
| 5,599,838 | A | * | 2/1997  | Sato et al. ................... 514/530 |
| 5,807,892 | A |   | 9/1998  | Klimko et al. |
| 5,852,050 | A |   | 12/1998 | Okumura et al. |
| 5,891,910 | A |   | 4/1999  | Buchmann et al. |
| 6,225,347 | B1 |  | 5/2001  | Buchmann et al. |

(Continued)

FOREIGN PATENT DOCUMENTS

EP  0 069 696  A2  1/1983

(Continued)

OTHER PUBLICATIONS

Hellhammer et al, Psychother Psychosom, 2001, 7, 6-16.*

(Continued)

*Primary Examiner*—Johann R Richter
*Assistant Examiner*—Abigail Fisher
(74) *Attorney, Agent, or Firm*—Sughrue Mion, PLLC

(57) ABSTRACT

A method of treating atopy-evoked pruritic symptoms by administering a prostaglandin derivative.

4 Claims, 4 Drawing Sheets

U.S. PATENT DOCUMENTS

| | | | |
|---|---|---|---|
| 6,329,539 B1 * | 12/2001 | Sato et al. | 554/214 |
| 6,395,786 B1 * | 5/2002 | Sato et al. | 514/573 |
| 6,506,789 B2 | 1/2003 | Arimura | |
| 6,617,353 B1 * | 9/2003 | Ito et al. | 514/557 |
| 6,635,678 B1 | 10/2003 | Kamm et al. | |
| 6,740,772 B1 | 5/2004 | Sato et al. | |
| 2004/0266880 A1 | 12/2004 | Sato et al. | |
| 2005/0009917 A1 | 1/2005 | Sato et al. | |
| 2005/0192357 A1 | 9/2005 | Arai et al. | |

FOREIGN PATENT DOCUMENTS

| | | |
|---|---|---|
| EP | 652211 A1 | 5/1995 |
| EP | 666256 A1 | 8/1995 |
| EP | 737676 A1 | 10/1996 |
| EP | 860430 A2 | 8/1998 |
| EP | 1 084 711 A1 | 3/2001 |
| EP | 1082961 A1 | 3/2001 |
| EP | 1083168 A1 | 3/2001 |
| EP | 1097922 A1 | 5/2001 |
| EP | 1170594 A2 | 1/2002 |
| EP | 1211242 A1 | 6/2002 |
| EP | 1 245 562 A1 | 10/2002 |
| EP | 1 312 601 A1 | 5/2003 |
| EP | 1 314 719 A1 | 5/2003 |
| EP | 1477170 A1 | 11/2004 |
| JP | 07-242622 A | 9/1995 |
| JP | 7-242622 A | 9/1995 |
| JP | 7-285929 A | 10/1995 |
| JP | 07-285929 A | 10/1995 |
| JP | 09-71539 A | 3/1997 |
| JP | 09-169638 A | 6/1997 |
| JP | 09-286775 A | 11/1997 |
| JP | 9-286775 A | 11/1997 |
| JP | 10-316564 A | 12/1998 |
| JP | 11-80031 A | 3/1999 |
| JP | 11-199478 A | 7/1999 |
| JP | 2000-273083 A | 10/2000 |
| JP | 2001-089443 A | 4/2001 |
| JP | 2001-122786 A | 5/2001 |
| JP | 2001-151749 A | 6/2001 |
| JP | 2001-220355 A | 8/2001 |
| WO | WO 85/00367 A1 | 1/1985 |
| WO | WO 85/02841 A1 | 7/1985 |
| WO | WO 89/00559 A1 | 1/1989 |
| WO | WO 93/06831 A1 | 4/1993 |
| WO | WO 96/16935 A1 | 6/1996 |
| WO | WO 97/45114 A1 | 12/1997 |
| WO | WO 98/27971 A1 | 7/1998 |
| WO | WO 99/25358 A1 | 5/1999 |
| WO | WO 99/62555 A1 | 12/1999 |
| WO | WO 9961029 A1 * | 12/1999 |
| WO | WO 9961419 A1 * | 12/1999 |
| WO | WO 00/31290 A1 | 6/2000 |
| WO | WO 00/32190 A1 | 6/2000 |
| WO | WO 01/19790 * | 3/2001 |
| WO | WO 01/19814 A2 | 3/2001 |
| WO | WO 01/49661 A1 | 7/2001 |
| WO | WO 02/16311 A1 | 2/2002 |
| WO | WO 02/20462 A1 | 3/2002 |
| WO | WO 02/45718 A1 | 6/2002 |
| WO | WO 02-45718 A1 | 6/2002 |
| WO | WO 03/070252 A1 | 8/2003 |

OTHER PUBLICATIONS

Grant et al., Advanced Drug Deliver Reviews, 2001, 48, 3-26.*
The Merck Manual, www.merck.com/mmhe/sec18/ch203/ch203c.html, 2006.*
Merriam-Webster Online Dictionary, www.merriam-webster.com/dictionary/preventing, 2005.*
Willoughby et al., The Lancet, 2000, 355, 646-648.*
Marsella, R. et al., "The ACVD task force on canine atopic dermatitis (XXII): nonsteroidal anti-inflammatory pharmacotherapy", Verteninary Immunology and Immunopathology, Sep. 20, 2001, vol. 81, No. 3-4, pp. 331-345.
Olivry, T. et al., "Treatment of canine atopic dermatitis with misoprostol, a prostaglandin E1 analogue: An open study", Database Embase [Online] XP002440431, 1997, abstract only.
Restriction Requirement dated Sep. 5, 2007 in U.S. Appl. No. 11/049,641.
Non-Final Office Action dated Jul. 24, 2007 in U.S. Appl. No. 10/492,948.
Response to Non-Final Office Action dated Oct. 24, 2007 in U.S. Appl. No. 10/492,948.
Angell et al., Role of the Parasite-derived Prostaglandin $D_2$ in the Inhibition of Epidermal Langerhans Cell Migration during Schistosomiasis Infection. J. Exp. Med., vol. 193, No. 10, May 21, 2001, pp. 1135-1147.
Lawrence S. Chan et al., "Expression of Interleukin-4 in the Epidermis of Transgenic Mice Results in a Pruritic Inflammatory Skin Disease: an Experimental Animal Model to Study Atopic Dermatitis", J. Invest. Dermatol., 2001, 117, pp. 977-983.
Final Office Action dated Jan. 15, 2008 in U.S. Appl. No. 10/492,948.
Final Office Action dated Feb. 1, 2008 in U.S. Appl. No. 11/049,641.
Angelika Buske-Kirschbaum et al., "Pyschobiological Aspects of Atopic Dermatitis: An Overview", Psycotherapy and Psychosomatics, 2001:70:6-16.
Sudha R. Vippagunta et al., "Crystalline Solids", Advanced Drug Delivery Reviews, (2001), 48, 3-26.
Response to Election of Species filed Dec. 5, 2007 in U.S. Appl. No. 11/049,641.
Amendment Under 37 C.F.R. § 1.116 filed Apr. 15, 2008 in U.S. Appl. No. 10/492,948.
Non-Final Office Action dated May 5, 2008 in U.S. Appl. No. 10/492,948.
Amendment Under 37 C.F.R. § 1.111, filed Oct. 24, 2007 in U.S. Appl. No. 10/492,948.
Amendment Under 37 C.F.R. § 1.111, filed Jun. 30, 2008 in U.S. Appl. No. 11/049,641.
Supplemental Amendment Under 37 C.F.R. § 1.111, filed Jul. 10, 2008 in U.S. Appl. No. 11/049,641.
Final Office Action dated Aug. 19, 2008 in U.S. Appl. No. 11/049,641.
Amendment Under 37 C.F.R. § 1.111, filed Oct. 6, 2008 in U.S. Appl. No. 10/492,948.
Final Office Action dated Dec. 16, 2008 in U.S. Appl. No. 10/492,948.
Request for Continued Examination and Amendment Under 37 CFR 1.114 in U.S. Appl. No. 11/049,641, filed Jan. 21, 2009.
Mark Abramovitz, et al., The Utilization of Recombinant Prostanoid Receptors to Determine the Affinities and Selectivities of Prostaglandins and Related Analogs, published in 2000.
Merck Manual, (http:www.merck.com/mmhe/sec18/ch203/ch203b.htm#sb203_1, obtained online on Apr. 17, 2009).
A Pons-Guiraud, "Dry Skin in Dermatology: A Complex Physiopathology", JEADV, vol. 21(Suppl. 2), pp. 1-4, 2007.
Non-Final Office Action dated Apr. 22, 2009, in U.S. Appl. No. 11/049,641.
Supplemental Response Under 37 CFR 1.111, and an executed Rule 132 Declaration of I. Arai dated Dec. 9, 2009, as filed in U.S. Appl. No. 11/049,641 on Dec. 11, 2009.
Amendment under 37 CFR 1.111 with attachment (Cell, vol. 83, 803-812 [1995]), and an executed Rule 132 Declaration of N. Nagahata dated Oct. 19, 2009, in U.S. Appl. No. 11/049,641, filed Oct. 22, 2009.

* cited by examiner

ANTIPRURITIC AGENT

TECHNICAL FIELD

This invention relates to pharmaceutical preparations for preventing or treating pruritic symptoms (the pharmaceutical preparations are hereunder sometimes referred to as antipruritics), more particularly to antipruritics effective in eliminating the itch sensation due to atopic symptoms.

BACKGROUND ART

Recent years have seen a rapid increase in the number of patients with pruritic symptoms as from atopic dermatitis, atopic conjunctivitis and senile xerosis. These diseases are accompanied by an intense itch sensation of obscure etiology and itch-evoked scratching behavior is believed to induce inflammations in mucous membranes or skin. Therefore, eliminating an itch sensation is crucial to the elimination of those symptoms.

Pharmaceutical preparations conventionally used to treat chronic dermatitis include steroids for external application, antihistamines and antiallergics. However, the use of steroids is restricted for the side effects they may cause as a result of prolonged continued use, and no antihistamines or antiallergics have been obtained that are completely satisfactory in terms of therapeutic efficacy.

Heretofore, antipruritics have been assessed by administering histamine, serotonin and other pruritogens into the skin of animals and measuring their itch-evoked scratching behavior. However, it was recently reported that the manifestation of an itch due to pruritic symptoms as in atopic dermatitis is not simply the reaction caused by histamine, etc. that are released from mast cells (J. Dermatological Science 25, 20-28, 2001).

Therefore, it is desired to develop antipruritics that depend on a new mechanism of action for preventing and treating pruritic symptoms as in atopic dermatitis.

A prostaglandin has been reported to be a prurigenic component (J. Am. Acad. Dermatol. 47, 28-32, 2002) but its use as an antipruritic is not known.

DISCLOSURE OF THE INVENTION

An object, therefore, of the present invention is to provide pharmaceutical preparations that depend on a new mechanism of action for preventing or treating pruritic symptoms, in particular, atopic symptoms.

With a view to attaining this object, the present inventors made an investigation adopting the method of assessment to be described later and found that certain kinds of prostaglandins had an outstanding antipruritic effect and were particularly effective in controlling the itch sensation accompanying atopic symptoms. The present invention has been accomplished on the basis of this finding.

Thus, according to one embodiment of the invention, there is provided a pharmaceutical preparation for preventing or treating pruritic symptoms which contains as an effective ingredient a prostaglandin derivative represented by formula [1]

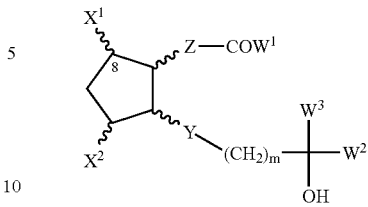

wherein $X^1$ and $X^2$ which are different from each other represent a hydrogen atom, a halogen atom or a hydroxyl group; Y is an ethylene group, a vinylene group or an ethynylene group; Z is the formula $(CH_2)_k A(CH_2)_h B(CH_2)_q$, $(CH_2)_k A(CH_2)_k A'(CH_2)_r$, $(CH_2)_k B(CH_2)_h B'(CH_2)_q$ or $(CH_2)_{k-1} B'(CH_2)_{q-1} A'$ wherein k is an integer of 1 to 4, h is an integer of 0 to 4, q is an integer 1 to 4, r is an integer of 0 to 4, and t is an integer of 0 to 2;

A and A' which may be the same or different represent an ethylene group, a vinylene group or an ethynylene group;

B and B' which may be the same or different represent an oxygen atom or a group represented by the formula $S(O)_u$ wherein u is an integer of 0 to 2;

$W^1$ is a hydroxyl group, a $C_{1-10}$ alkyloxy group, a $C_{3-10}$ cycloalkyloxy group, an aryloxy group or an arylalkyloxy group;

$W^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl group substituted by a $C_{3-10}$ cycloalkyl group, or a group represented by the formula

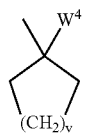

wherein $W^4$ is a $C_{1-10}$ alkyl group, a $C_{2-10}$ alkenyl group, a $C_{2-10}$ alkynyl group or a $C_{1-5}$ alkyl group substituted by $C_{3-10}$ cycloalkyl group(s); v is an integer of 0 to 4;

$W^3$ is a hydrogen atom or a methyl group, or $W^3$ when taken together with $W^2$ and the adjacent carbon atom forms a $C_{3-10}$ cycloalkyl group; m is 0 or 1, a pharmaceutically acceptable salt thereof or a hydrate thereof.

According to another embodiment of the invention, there is provided a pharmaceutical preparation for preventing or treating atopic symptoms which contains as an effective ingredient a prostaglandin derivative represented by formula [1]

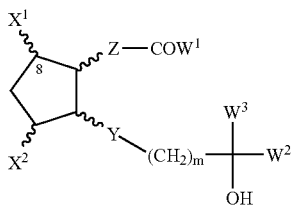

wherein $X^1$ and $X^2$ which are different from each other represent a hydrogen atom, a halogen atom or a hydroxyl group; Y is an ethylene group, a vinylene group or an ethynylene group; Z is the formula $(CH_2)_k A(CH_2)_h B(CH_2)_q$, $(CH_2)_k A(CH_2)_r A'(CH_2)_t$, $(CH_2)_k B(CH_2)_h B'(CH_2)_q$ or $(CH_2)_{k-1} B'(CH_2)_{q-1} A'$ wherein k is an integer of 1 to 4, h is an integer of 0 to 4, q is an integer 1 to 4, r is an integer of 0 to 4, and t is an integer of 0 to 2;

A and A' which may be the same or different represent an ethylene group, a vinylene group or an ethynylene group;

B and B' which may be the same or different represent an oxygen atom or a group represented by the formula $S(O)_u$ wherein u is an integer of 0 to 2;

$W^1$ is a hydroxyl group, a $C_{1-10}$ alkyloxy group, a $C_{3-10}$ cycloalkyloxy group, an aryloxy group or an arylalkyloxy group;

$W^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl group substituted by $C_{3-10}$ cycloalkyl group(s), or a group represented by the formula

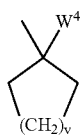

wherein $W^4$ is a $C_{1-10}$ alkyl group, a $C_{2-10}$ alkenyl group, a $C_{2-10}$ alkynyl group or a $C_{1-5}$ alkyl group substituted by $C_{3-10}$ cycloalkyl group(s); v is an integer of 0 to 4; $W^3$ is a hydrogen atom or a methyl group, or $W^3$ when taken together with $W^2$ and the adjacent carbon atom forms a $C_{3-10}$ cycloalkyl group; m is 0 or 1, a pharmaceutically acceptable salt thereof or a hydrate thereof.

According to yet another embodiment of the invention, there is provided a pharmaceutical preparation for preventing or treating pruritic or atopic symptoms which contains as an effective ingredient a prostaglandin derivative represented by formula [1], provided that 7-[(1R,2R,3R,5R)-5-chloro-2-[(1E,3S)-3-cyclohexyl-3-hydroxy-1-propenyl]-3-hydroxy-cyclopentyl]-(5Z)-5-heptenic acid is excluded, a pharmaceutically acceptable salt thereof or a hydrate thereof.

According to still another embodiment of the invention, there is provided a pharmaceutical preparation for preventing or treating pruritic or atopic symptoms which contains as an effective ingredient a prostaglandin derivative represented by formula [1] wherein $X^1$ is a halogen atom, $X^2$ is a hydroxyl group and Y is an ethynylene group, a pharmaceutically acceptable salt thereof or a hydrate thereof.

According to a still further embodiment of the invention, there is provided a pharmaceutical preparation for preventing or treating pruritic or atopic symptoms which contains as an effective ingredient a prostaglandin derivative represented by formula [1] wherein $X^1$ is a halogen atom, $X^2$ is a hydroxyl group and Y is a vinylene group, a pharmaceutically acceptable salt thereof or a hydrate thereof.

According to yet another embodiment of the invention, there is provided a pharmaceutical preparation for preventing or treating pruritic or atopic symptoms which contains as an effective ingredient a prostaglandin derivative represented by formula [1] wherein $W^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl group substituted by $C_{3-10}$ cycloalkyl group(s), or a group represented by the formula

wherein $W^4$ is a $C_{1-10}$ alkyl group, a $C_{2-10}$ alkenyl group, a $C_{2-10}$ alkynyl group or a $C_{1-5}$ alkyl group substituted by $C_{3-10}$ cycloalkyl group(s); v is an integer of 0 to 4; $W^3$ is a hydrogen atom or a methyl group, a pharmaceutically acceptable salt thereof or a hydrate thereof.

According to a further embodiment of the invention, there is provided such a pharmaceutical preparation for preventing or treating atopic symptoms wherein the atopic symptoms are those in atopic dermatitis or atopic conjunctivitis.

According to a still further embodiment of the invention, there is provided such a pharmaceutical preparation for preventing or treating pruritic or atopic symptoms which is an agent for external application.

BEST MODE FOR CARRYING OUT THE INVENTION

Figure 1:
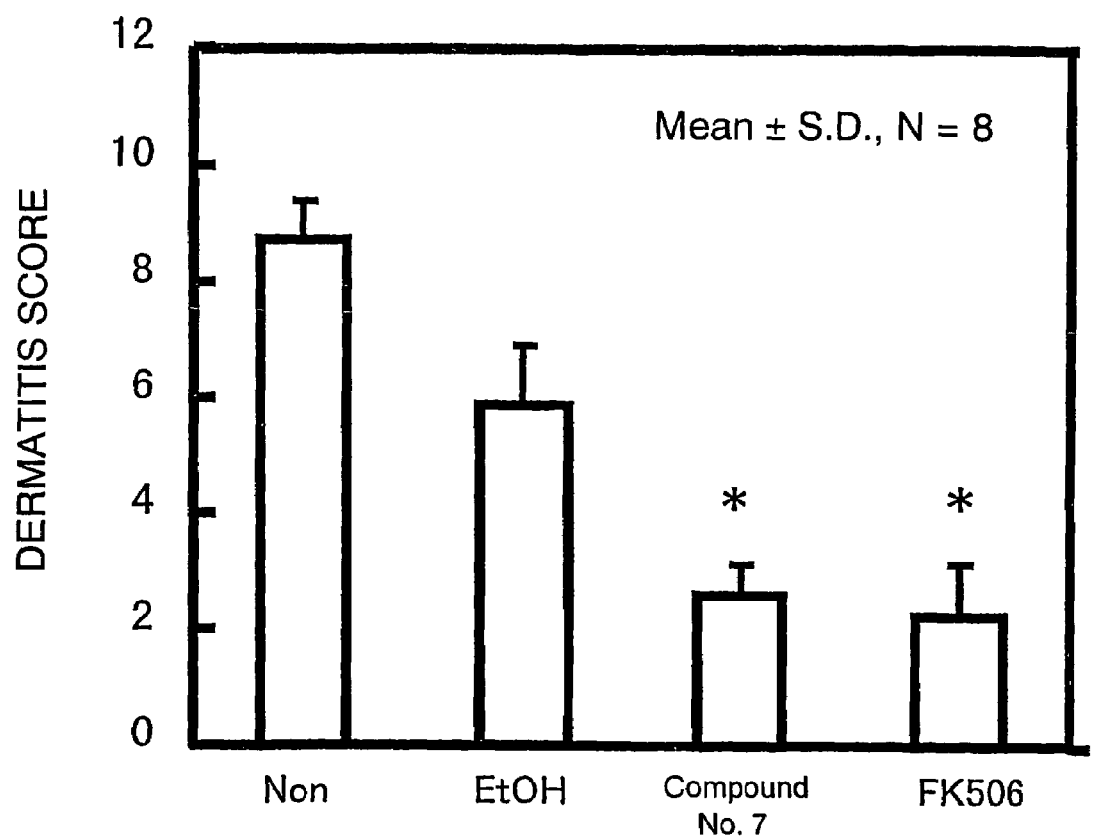
FIG. 1 shows the results with dermatitic symptoms (dermatitis scores) as observed at 4 weeks after drug administration, in which Non refers to no treatment, EtOH ethanol, FK506 tacrolimus, and * means p<0.05.

The inventors assessed the antipruritic effect of various pharmaceutical preparations on itch-evoked but spontaneous scratching behavior by measuring the itch-evoked scratching behavior of NC/Nga mice that would spontaneously develop an atopic dermatitis-like skin disease.

The numbers of scratchings done by the individual animals during 24-hr periods before and after the dermal application of pharmaceutical preparations were compared to confirm the outstanding efficacy of prostaglandins represented by formula [1].

The antipruritics of the invention are described below.

The invention is characterized as containing prostaglandin derivatives of the formula [1], pharmaceutically acceptable salts thereof or hydrates thereof as an effective ingredient.

In the formula [1], the halogen atom means a fluorine atom, a chlorine atom, a bromine atom or an iodine atom.

The vinylene group means a cis- or trans-vinylene group.

The $C_{1-10}$ alkyloxy group represents linear or branched alkyloxy groups having 1 to 10 carbon atoms, which include, for example, a methoxy group, an ethoxy group, a propoxy group, an isopropoxy group, a butoxy group, a sec-butoxy group, a tert-butoxy group, a pentyloxy group, a tert-pentyloxy group, a 5-methylhexyloxy group, an octyloxy group, a decyloxy group, etc.

Examples of the $C_{3-10}$ cycloalkyloxy group include a cyclopropyloxy group, a cyclobutyloxy group, a cyclopentyloxy group, a cyclohexyloxy group, a cycloheptyloxy group, a cyclononyloxy group, etc.

Examples of the aryloxy group include a phenoxy group, a bromophenoxy group, a chlorophenoxy group, a tolyloxy group, a cumenyloxy group, a methoxyphenoxy group, etc.

Examples of the arylalkyloxy group include a benzyloxy group, a bromobenzyloxy group, a chlorobenzyloxy group, a nitrobenzyloxy group, a dinitrobenzyloxy group, a methoxybenzyloxy group, a phenethyloxy group, a phenylpropyloxy group, a phenylpentyloxy group, etc.

The $C_{1-10}$ alkyl group represents linear or branched alkyl groups having 1 to 10 carbon atoms, which include, for example, a methyl group, an ethyl group, a propyl group, an isopropyl group, a butyl group, a sec-butyl group, a tert-butyl group, a pentyl group, a tert-pentyl group, an isohexyl group, a heptyl group, an octyl group, a decyl group, etc.

The $C_{2-10}$ alkenyl group means those linear or branched alkyl groups with 2 to 10 carbon atoms which have one or more double bonds in desired positions and they may be exemplified by a vinyl group, an allyl group, a 1-propenyl group, an isopropenyl group, a 3-butenyl group, a 1,3-butadienyl group, a 7-octenyl group, etc.

The $C_{2-10}$ alkynyl group means those linear or branched alkyl groups with 2 to 10 carbon atoms which have one or more triple bonds in desired positions and may be exemplified by an ethynyl group, a 2-propynyl group, a 2-pentynyl group, a 4-octynyl group, etc.

Examples of the $C_{3-10}$ cycloalkyl group include unsubstituted cycloalkyl groups such as a cyclopropyl group, a cyclobutyl group, a cyclopentyl group, a cyclohexyl group, a cycloheptyl group and a cyclononyl group, as well as those cycloalkyl groups having one or more substituents selected from among halogen atoms, $C_{1-10}$ alkyl groups, $C_{1-10}$ alkyloxy groups, etc. which are exemplified by a 4-fluorocyclohexyl group, a 4,4-difluorocyclohexyl group, a 4-methoxycyclohexyl group, a 2-methylcyclohexyl group, a 4-trifluoromethylcyclohexyl group, etc.

Examples of the $C_{1-5}$ alkyl group substituted by $C_{3-10}$ cycloalkyl group(s) include a cyclopropylmethyl group, a cyclobutylethyl group, a cyclopentylmethyl group, a cyclohexylmethyl group, a cycloheptylmethyl group, a cyclononylbutyl group, a 4-fluorocyclohexylmethyl group, etc.

The pharmaceutically acceptable salt may be exemplified by salts with alkali metals such as sodium and potassium, salts with alkaline earth metals such as calcium and magnesium, and salts with ammonia, methylamine, dimethylamine, cyclopentylamine, benzylamine, piperidine, monoethanolamine, diethanolamine, monomethylmonoethanolamine, tromethamine, lysine, tris(hydroxymethyl)aminomethane, etc.

If Z is the formula $(CH_2)_k A(CH_2)_h B(CH_2)_q$, preferably, k+h+q=3, and more preferably, k=1, h=1 and q=1. If Z is the formula $(CH_2)_k A(CH_2)_r A'(CH_2)_t$, preferably, k+r+t=2, and more preferably, k=1, r=1 and t=0. If Z is the formula $(CH_2)_k B(CH_2)_h B'(CH_2)_q$, preferably, k+h+q=4, and more preferably, k=1, h=2 and q=1. If Z is the formula $(CH_2)_{k-1} B' (CH_2)_{q-1} A'$, preferably, k+q=5, and more preferably, k=2 and q=3.

Some of the prostaglandin derivatives which serve as the effective ingredient in the present invention are known compounds disclosed in the following official gazettes:

WO94/02457, WO94/08959, WO95/18101, WO99/61029, WO99/61419, WO01/19790, U.S. Pat. No. 5,807,892, JP 2-502009 A, JP 6-192218 A, JP 7-242622 A, JP 7-242623 A, JP 7-233144 A, JP 7-285929 A, JP 8-208599 A, JP 9-286775 A, JP 58-8059 A, JP 60-501813 A, JP 61-500787 A, JP 2000-95755 A, JP 2000-128858 A, JP 2000-273083 A, JP 2001-122786 A, JP 2001-89443 A, JP 2001-135944 A, and JP 2001-151749 A.

Note that prostaglandin derivatives represented by the following formula

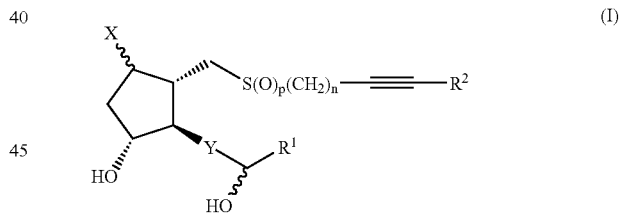

wherein X is an α- or β-substituted halogen atom, Y is an ethylene group, a vinylene group or an ethynylene group, $R^1$ is a $C_{3-10}$ cycloalkyl group, a $C_{3-10}$ cycloalkyl group substituted by $C_{1-4}$ linear or branched alkyl group(s), or a $C_{4-13}$ cycloalkylalkyl group, $R^2$ is a group represented by $CO_2R^3$, wherein $R^3$ is a hydrogen atom, a $C_{1-4}$ linear or branched alkyl group or a $C_{2-4}$ linear or branched alkenyl group, n is an integer of 1 to 4, and p is 0, 1 or 2 can be produced by processes according to reaction schemes 1 and 2.

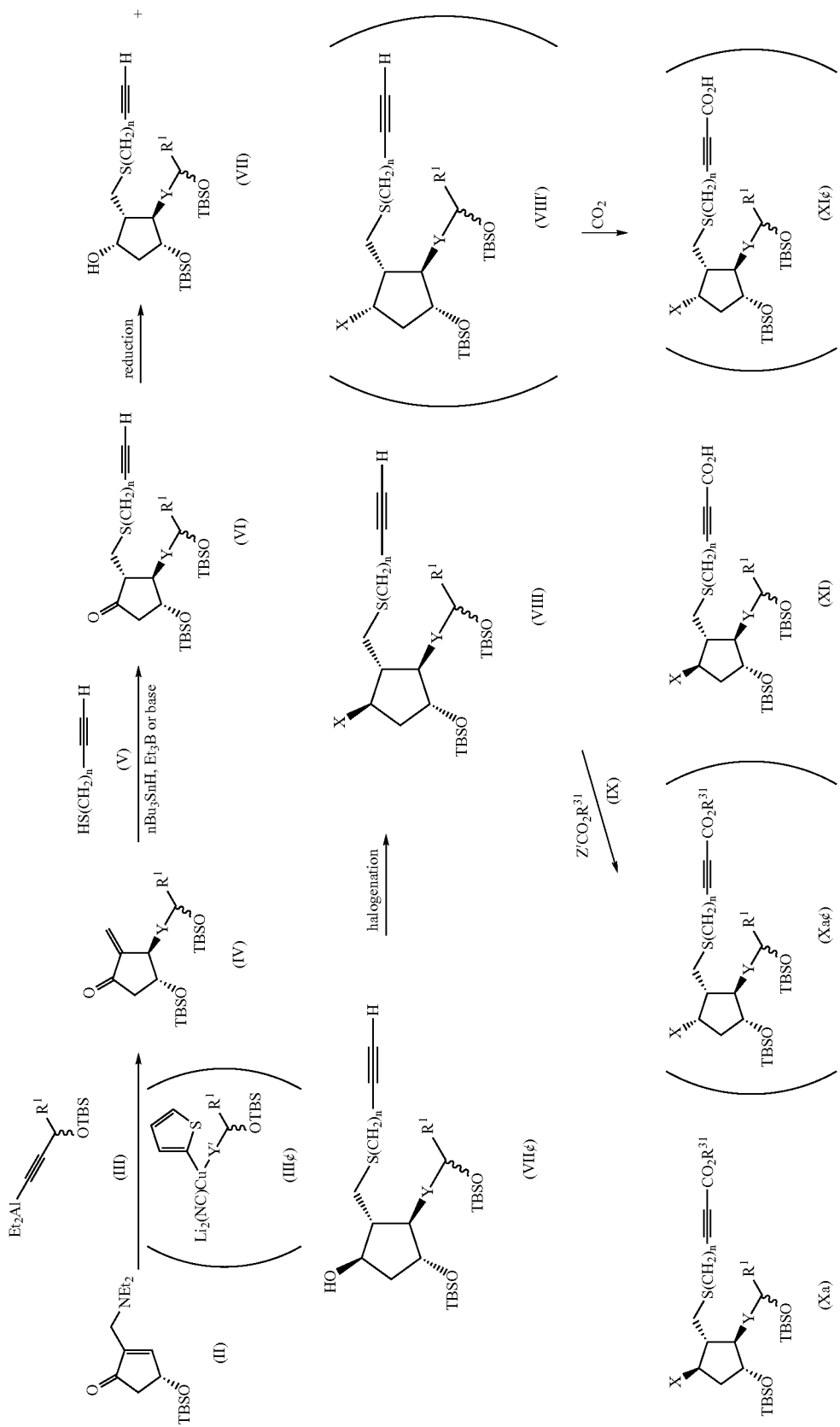

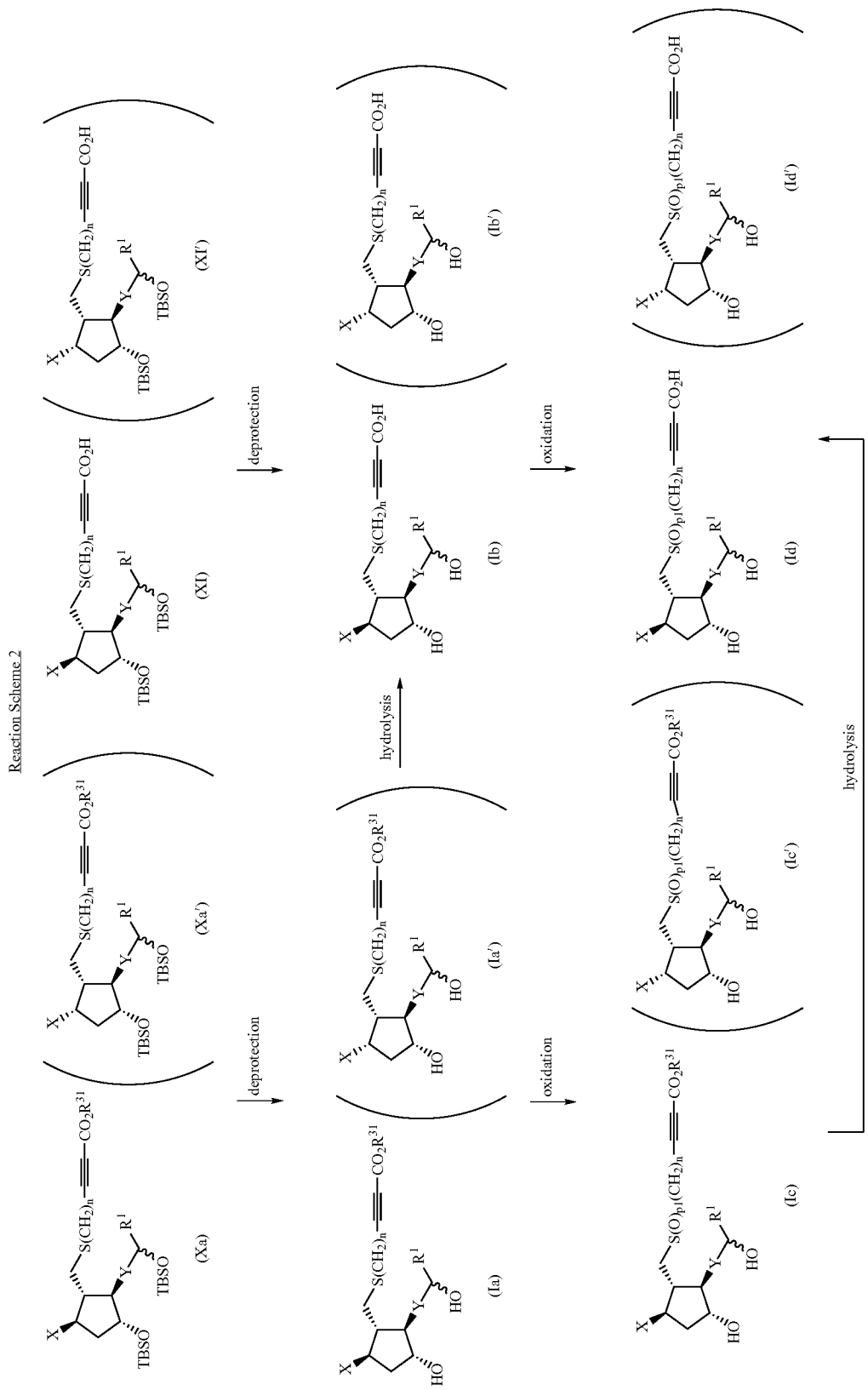

(in the above reaction schemes, TBS represents a tert-butyldimethylsilyl group, Y' represents an ethylene group or a vinylene group, $R^{31}$ represents a $C_{1-4}$ alkyl group or a $C_{2-4}$ alkenyl group, p1 represents 1 or 2, Z' represents a halogen atom, and X, Y, $R^1$ and n have the same meanings as defined above.)

The two reaction schemes are explained below:

(1) First, according to the method of Satoh et al. [Journal of Organic Chemistry (J. Org. Chem.), vol. 53, p. 5590 (1988)], a known compound of formula (II) is reacted with 0.8 to 2.0 equivalent amounts of a compound represented by formula (III) or (III') in an inert solvent (e.g. benzene, toluene, tetrahydrofuran, diethyl ether, methylene chloride or n-hexane) at −78 to 30° C., to give a stereospecific compound of formula (IV). In order to obtain a compound where Y is an ethylene group or a vinylene group (i.e. Y is Y'), a compound of formula (III') is employed and reaction is performed at −78 to 0° C.; in order to obtain a compound where Y is an ethynylene group, a compound of formula (III) is employed and reaction is performed at 0 to 30° C.

(2) The compound of formula (IV) is reacted with 1 to 6 equivalent amounts of a compound represented by formula (V) in an organic solvent (e.g. benzene, toluene, xylene, n-hexane, n-pentane or acetone) at −78 to 100° C., optionally employing 0.05 to 2 equivalent amounts of a radical generator (e.g. azobisisobutyronitrile, azobiscyclohexanecarbonitrile, benzoyl peroxide or triethylborane), further optionally employing 1 to 5 equivalent amounts of a radical reducing agent (e.g. tributyltin hydride, triphenyltin hydride, dibutyltin hydride or diphenyltin hydride), thereby giving a compound of formula (VI). In a certain case, a compound of formula (VI) can also be obtained by performing the reaction in an organic solvent (e.g. benzene, toluene, xylene, n-hexane, n-pentane or acetone) at −78 to 100° C. employing 0.05 to 2 equivalent amounts of a base (e.g. an organic amine such as triethylamine, diisopropylamine, pyridine or dimethylaniline, or a base resin such as polyvinylpyrrolidone, diisopropylaminomethyl-polystyrene or (piperidinomethyl)polystyrene).

(3) The compound of formula (VI) is reacted with 0.5 to 5 equivalent amounts of a reducing agent such as potassium borohydride, sodium borohydride, sodium cyanoborohydride, lithium tri-sec-butyl borohydride or diisobutylaluminum hydride-BHT (2,6-di-tert-butyl-p-cresol) in an organic solvent (e.g. tetrahydrofuran, diethyl ether, ethyl alcohol, methyl alcohol or toluene) at −78 to 40° C. to give compounds of formulas (VII) and (VII'). These compounds of formulas (VII) and (VII') can be purified by a commonly employed separation technique such as column chromatography.

(4) The compound of formula (VII) (or formula (VII')) is mesylated or tosylated with, for example, 1 to 6 equivalent amounts of methanesulfonyl chloride or p-toluenesulfonyl chloride in a suitable solvent such as pyridine at −20 to 40° C., optionally in the presence of 0.8 to 6 equivalent amounts of 4-dimethylaminopyridine, followed by chlorination with 1 to 16 equivalent amounts of tetra-n-butylammonium chloride to give a compound of formula (VIII) (or formula (VIII')) (X is a chlorine atom). Bromination and fluorination can also be performed by ordinary methods. For example, bromination can be obtained by reacting 1 to 10 equivalent amounts of carbon tetrabromide in acetonitrile in the presence of 1 to 10 equivalent amounts each of triphenylphosphine and pyridine. Fluorination may, for example, be obtained by reacting 5 to 20 equivalent amounts of diethylaminosulfate trifluoride (DAST) in methylene chloride.

(5) The compound of formula (VIII) (or formula (VIII')) is reacted with a base (e.g. an alkyl lithium such as n-butyl-lithium) at a temperature between −78° C. and room temperature in a suitable inert organic solvent (e.g. tetrahydrofuran or diethyl ether) and thereafter reacted with a compound of formula (IX) at −78 to 40° C. to give a compound of formula (Xa) (or formula (Xa')); if the formula (IX) is replaced by carbon dioxide as the reactant, a compound of formula (XI) (or formula (XI')) can be obtained.

(6) The compound of formula (Xa) (or formula (Xa')) is freed of the hydroxyl protecting tert-butyldimethylsilyl group in methanol, ethanol, acetonitrile or a mixed solvent thereof or a mixture thereof with water under ordinary conditions employing hydrofluoric acid, pyridinium poly(hydrogenfluoride), hydrochloric acid, etc. so as to give a PG derivative of formula (Ia) (or formula (Ia')) according to the present invention.

(7) By hydrolyzing the compound of formula (Ia) (or formula (Ia')) through reaction with an enzyme in a buffer solution such as a phosphate buffer or a Tris-HCl buffer, optionally employing an organic solvent (a water-miscible one such as acetone, methanol or ethanol), a PG derivative of formula (Ib) (or formula (Ib')) claimed in the invention can be obtained. Exemplary enzymes are those produced by microorganisms (e.g. enzymes produced by microorganisms of *Candida* sp. and *Pseudomonas* sp.) and those prepared from animal organs (e.g. enzymes prepared from swine liver and pancreas). To mention specific examples of commercial enzymes, they include lipase VII (product of Sigma, derived from a microorganism of *Candida* sp.), lipase AY (product of Amano Pharmaceutical Co., Ltd., derived from a microorganism of *Candida* sp.), lipase PS (product of Amano Pharmaceutical Co., Ltd., derived from a microorganism of *Pseudomonas* sp.), lipase MF (product of Amano Pharmaceutical Co., Ltd., derived from a microorganism of *Pseudomonas* sp.), PLE (product of Sigma, prepared from swine liver), lipase II (product of Sigma, prepared from swine pancreas), and lipoprotein lipase (product of Tokyo Kasei Kogyo Co., Ltd., prepared from swine pancreas).

The amount of the enzyme to be used may be chosen as appropriate for its potency and the amount of its substrate [formula (Ia) (or formula (Ia'))] and the usual amount is 0.1 to 20 times the weight of the substrate. The reaction temperature is 25 to 50° C., preferably 30 to 40° C.

A PG derivative of formula (Ib) (or formula (Ib')) claimed in the invention may be obtained by hydrolyzing the compound of formula (Ia) (or formula (Ia')) with a base in a solvent commonly employed in hydrolysis. Exemplary bases that can be employed are lithium hydroxide and potassium carbonate, and exemplary solvents include acetonitrile, acetone, methanol, ethanol, water and mixtures thereof.

A PG derivative of formula (Ib) (or formula (Ib')) claimed in the invention can also be obtained by deprotecting the compound of formula (XI) (or formula (XI')) as in (6) above.

(8) The compound of formula (Ia) (or formula (Ia')) is reacted with an oxidizing agent such as sodium metaperiodate, hydrogen peroxide, peracetic acid, m-chloroperbenzoic acid and tert-butyl hydroperoxide in diethyl ether, methanol, ethanol, methylene chloride, water or mixtures thereof at −20 to 50° C. to give a PG derivative of formula (Ic) (or formula (Ic')) claimed in the invention.

(9) By hydrolyzing the compound of formula (Ic) (or formula (Ic')) as in (7) above, a PG derivative of formula (Id) (or formula (Id')) claimed in the invention is obtained. A PG derivative of formula (Id) (or formula (Id')) claimed in the invention can also be obtained by oxidizing the formula (Ib) (or formula (Ib')) as in (8) above.

The following compounds can be listed as representative compounds of the formula [1] claimed in the invention.

TABLE 1

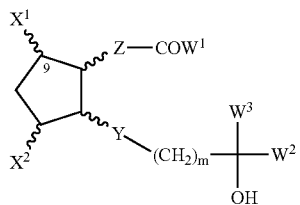

[1]

| Compound No. | X1 | X2 | Y | A | B | m | k | h | q | u | W1 | W2 | W3 | 8-position | 9-position | 11-position | 12-position | OH |
|---|---|---|---|---|---|---|---|---|---|---|---|---|---|---|---|---|---|---|
| 1 | Cl | HO | CH2CH2 | Z-CH=CH | S | 0 | 1 | 1 | 1 | 0 | OMe | cyc6 | H | α | β | α | β | α |
| 2 | Cl | HO | CH2CH2 | Z-CH=CH | S | 0 | 1 | 1 | 1 | 0 | OH | cyc6 | H | α | β | α | β | α |
| 3 | Cl | HO | E-CH=CH | Z-CH=CH | O | 0 | 1 | 1 | 1 |  | OH | cyc6 | H | α | β | α | β | α |
| 4 | Cl | HO | C≡C | Z-CH=CH | O | 0 | 1 | 1 | 1 |  | OtBu | cyc6 | H | α | β | α | β | α |
| 5 | Cl | HO | C≡C | CH2CH2 | O | 0 | 1 | 1 | 1 |  | OtBu | cyc6 | H | α | β | α | β | α |
| 6 | Cl | HO | C≡C | CH2CH2 | S | 0 | 1 | 1 | 1 | 0 | OMe | cyc6 | H | α | β | α | β | α |
| 7 | Cl | HO | C≡C | CH2CH2 | S | 0 | 1 | 1 | 1 | 0 | OH | cyc6 | H | α | β | α | β | α |
| 8 | Cl | HO | C≡C | Z-CH=CH | O | 0 | 1 | 1 | 1 |  | OH | cyc6 | H | α | β | α | β | α |
| 9 | H | HO | C≡C | CH2CH2 | S | 0 | 1 | 1 | 1 | 0 | OH | cyc6 | H | α |  | α | β | α |
| 10 | Cl | HO | C≡C | C≡C | O | 0 | 1 | 1 | 1 |  | OH | cyc6 | H | α | β | α | β | α |
| 11 | Cl | HO | CH2CH2 | Z-CH=CH | O | 0 | 1 | 1 | 1 |  | OH | cyc6 | H | α | β | α | β | α |
| 12 | Cl | HO | E-CH=CH | CH2CH2 | S | 0 | 1 | 1 | 1 | 0 | OH | cyc6 | H | α | β | α | β | α |

E-CH=CH: trans-vinylene group
Z-CH=CH: cis-vinylene group
cyc6: cyclohexyl group

TABLE 2

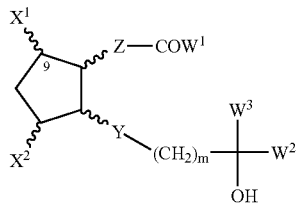

[1]

| Compound No. | X1 | X2 | Y | A | A' | m | k | r | t | W1 | W2 | W3 | 8-position | 9-position | 11-position | 12-position | OH |
|---|---|---|---|---|---|---|---|---|---|---|---|---|---|---|---|---|---|
| 13 | Cl | HO | E-CH=CH | CH2CH2 | C≡C | 0 | 1 | 1 | 0 | OMe | cyc5m | H | α | α | α | β | α |
| 14 | Cl | HO | C≡C | CH2CH2 | C≡C | 0 | 1 | 2 | 0 | OH | cyc6 | H | α | β | α | β | α |
| 15 | Cl | HO | C≡C | CH2CH2 | C≡C | 0 | 1 | 1 | 0 | OH | cyc6 | H | α | β | α | β | α |
| 16 | Cl | HO | C≡C | CH2CH2 | E-CH=CH | 0 | 1 | 1 | 0 | OMe | cyc6 | H | α | β | α | β | α |
| 17 | Cl | HO | C≡C | CH2CH2 | E-CH=CH | 0 | 1 | 1 | 0 | OiPr | cyc6 | H | α | β | α | β | α |
| 18 | Cl | HO | C≡C | CH2CH2 | E-CH=CH | 0 | 1 | 1 | 0 | OtBu | cyc6 | H | α | β | α | β | α |
| 19 | Cl | HO | C≡C | CH2CH2 | C≡C | 0 | 1 | 1 | 0 | OtBu | cyc6 | H | α | β | α | β | α |
| 20 | Cl | HO | C≡C | CH2CH2 | C≡C | 0 | 1 | 1 | 1 | OMe | Me-cyc6 | H | α | β | α | β | α |

Z-CH=CH: cis-vinylene group
E-CH=CH: trans-vinylene group
cyc6: cyclohexyl group
Me-cyc6: 2-methylcyclohexyl group
cyc5m: cyclopentylmethyl group

TABLE 3

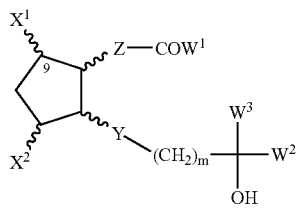

[1]

| Compound No. | X1 | X2 | Y | B | B' | m | k | h | q | u | W1 | W2 | W3 | 8-position | 9-position | 11-position | 12-position | OH |
|---|---|---|---|---|---|---|---|---|---|---|---|---|---|---|---|---|---|---|
| 21 | Cl | HO | C≡C | S | O | 0 | 1 | 2 | 1 | 0 | OMe | cyc6 | H | α | β | α | β | α |
| 22 | Cl | HO | C≡C | S | O | 0 | 1 | 2 | 1 | 0 | OH | cyc6 | H | α | β | α | β | α |
| 23 | Cl | HO | C≡C | S | S | 0 | 1 | 2 | 1 | 0 | OMe | cyc6 | H | α | β | α | β | α |
| 24 | Cl | HO | C≡C | S | S | 0 | 1 | 2 | 1 | 0 | OMe | cyc6 | H | α | α | α | β | α |
| 25 | Cl | HO | C≡C | S | S | 0 | 1 | 2 | 1 | 0 | OH | cyc6 | H | α | β | α | β | α |
| 26 | Cl | HO | C≡C | S | O | 0 | 1 | 2 | 1 | 0 | OMe | diF-cyc6 | H | α | β | α | β | α |
| 27 | Cl | HO | C≡C | S | O | 0 | 1 | 2 | 1 | 0 | OH | diF-cyc6 | H | α | β | α | β | α |
| 28 | Cl | HO | C≡C | S | O | 0 | 1 | 2 | 1 | 0 | OMe | CF3-cyc6 | H | α | β | α | β | α |
| 29 | Cl | HO | C≡C | S | O | 0 | 1 | 2 | 1 | 0 | OH | CF3-cyc6 | H | α | β | α | β | α |
| 30 | Cl | HO | C≡C | S | S | 0 | 1 | 3 | 1 | 0 | OMe | cyc6 | H | α | β | α | β | α | cyc6: cyclohexyl group
diF-cyc6: difluorocyclohexyl group
CF3-cyc6: 4-trifluoromethylcyclohexyl group

TABLE 4

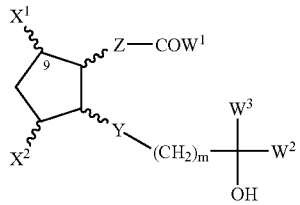

[1]

| Compound No. | X1 | X2 | Y | A' | B' | m | k | q | u | W1 | W2 | W3 | 8-position | 9-position | 11-position | 12-position | OH |
|---|---|---|---|---|---|---|---|---|---|---|---|---|---|---|---|---|---|
| 31 | Cl | HO | C≡C | CH2CH2 | S | 0 | 2 | 3 | 0 | OMe | cyc6 | H | α | β | α | β | α |
| 32 | Cl | HO | C≡C | CH2CH2 | S | 0 | 2 | 3 | 0 | OH | cyc6 | H | α | β | α | β | α |
| 33 | Cl | HO | E-CH=CH | CH2CH2 | S | 0 | 1 | 4 | 0 | OMe | cyc6 | H | α | β | α | β | α |
| 34 | Cl | HO | E-CH=CH | CH2CH2 | S | 0 | 4 | 1 | 0 | OMe | cyc6 | H | α | β | α | β | α |
| 35 | Cl | HO | E-CH=CH | CH2CH2 | S | 0 | 3 | 2 | 0 | OMe | cyc6 | H | α | β | α | β | α |
| 36 | Cl | HO | E-CH=CH | CH2CH2 | S | 0 | 2 | 3 | 0 | OH | cyc6 | H | α | β | α | β | α |
| 37 | Cl | HO | CH2CH2 | CH2CH2 | S | 0 | 2 | 3 | 0 | OMe | cyc6 | H | α | β | α | β | α |
| 38 | Cl | HO | CH2CH2 | CH2CH2 | S | 0 | 2 | 3 | 0 | OH | cyc6 | H | α | β | α | β | α |
| 39 | Cl | HO | C≡C | C≡C | S | 0 | 2 | 3 | 0 | OH | cyc6 | H | α | β | α | β | α |
| 40 | Cl | HO | C≡C | CH2CH2 | S | 0 | 2 | 1 | 0 | OH | cyc6 | H | α | β | α | β | α |

E-CH=CH: trans-vinylene group
cyc6: cyclohexyl group

As long as they can relieve or eliminate an itch sensation, the antipruritics of the invention are not limited in any way but they are particularly effective against the atopy-evoked itching. From this viewpoint, the antipruritics of the invention encompass pharmaceutical preparations for preventing or treating atopic symptoms.

In the invention, the term "pruritic symptoms" means those symptoms which involve circumscribed or generalized itching and associated inflammations on the skin and mucous membranes. Examples include scabies, urticaria, eczema, xerosis (senile xeroderma and asteatotic eczema), psoriasis, dermal pruritus, and prurigo.

In the invention, the term "atopic symptoms" means those symptoms which involve atopy-evoked, circumscribed or generalized itching and associated inflammations on the skin and mucous membranes; in other words, the term refers to atopy-evoked pruritic symptoms (including nervous pruritus). Examples include atopic dermatitis and atopic conjunctivitis.

In the invention, the term "atopic dermatitis" refers to a disorder that involves itching eczema as a principal lesion which undergoes repeated exacerbation and remission; this is highly likely to develop in individuals predisposed to atopy.

The antipruritics of the invention can be administered either orally, parenterally or topically.

The dose to be administered of the effective ingredient in the antipruritics of the invention can be adjusted as appropriate for the body weight of the patient, his or her age, sex, etc.

Usually, the dosage is 1 ng to 10 mg, preferably 0.1 to 100 μg, per administration and one to several administrations are tolerated per day.

The antipruritics of the invention can be prepared as pharmaceutical compositions employing the effective ingredient in combination with carriers, vehicles and other additives that are employed in ordinary pharmaceutical formulation procedures.

Exemplary carriers and vehicles for pharmaceutical formulation procedures include water, ethanol, lactose, microcrystalline cellulose, liquid paraffin, hydrogenated oils, beeswax, squalane, stearyl alcohol, ethylene glycol and others that are in common use.

Exemplary additives are commonly employed ingredients including disintegrants (e.g. starch), binders (hydroxypropyl cellulose and low-substituted hydroxypropyl cellulose), lubricants (e.g. talc and glycerol stearate), antioxidants, preservatives (e.g. parabens), coating agents (e.g. gelatin and hydroxypropyl cellulose), coloring agents, flavoring/odorizing agents, skin color lightening agents (e.g. sodium ellagate), surfactants (e.g. sorbitan fatty acid esters), plasticizers, humectants (e.g. glycerin, propylene glycol, polyethylene glycol and hyaluronic acid), etc.

The antipruritics of the invention can be administered in various dosage forms such as those for internal application, injections and those for external application (nasal drops and eye drops), as specifically exemplified by tablets, granules, powders, capsules, liquids, gels, plasters, ointments, creams, cataplasms and aerosols.

Dosage forms for external application are preferred for the various advantages they have, such as direct applicability to the diseased area, ease of application and a reduced possibility for the occurrence of systemic side effects.

Dosage forms "for external application" include liquids for external application, aerosols, powders for external application, ointments, creams, gels, plasters, cataplasms, etc.

The following examples and test examples are provided for the purpose of further illustrating the present invention but are in no way to be taken as limiting. Various alterations and modifications can be made by the skilled artisan on the basis of the foregoing description of the invention and are also encompassed by the invention.

Unless otherwise noted, the drug concentration (%) means w/v % (weight/volume %).

Example 1

The ingredients listed below were weighed and mixed uniformly; then, purified water and ethanol were added in the volumes indicated below to make 1000 ml of a liquid.

| | |
|---|---|
| Compound No. 7 | 0.1 g |
| Ethanol | 200 ml |
| Purified water | 800 ml |

Example 2

The ingredients listed below were weighed and emulsified uniformly; then, a flavoring agent was added to make 500 g of a cream.

| | |
|---|---|
| Compound No. 3 | 0.5 g |
| Carbinoxamine maleate | 5 g |
| Sodium ellagate | 5 g |
| Sodium hyaluronate | 3 g |
| Methyl paraben | 2 g |

| -continued | |
|---|---|
| Purified water | 218.5 g |
| Liquid paraffin(#70) | 50 g |
| Squalane | 100 g |
| Cetostearyl alcohol | 60 g |
| Beeswax | 20 g |
| Glycerol monostearate | 15 g |
| Sorbitan monolaurate | 20 g |
| Propyl paraben | 1 g |

Test Example 1

Effect on the Spontaneous, Itch-Evoked Scratching Behavior of NC Mice (Method)

About 20-week old NC/Nga mice each weighing about 30 g and manifesting atopic dermatitis were purchased from SLC and subjected to the following experiment. A magnet was buried in both hind paws of each mouse and by detecting its magnetism, the movement of the paws was measured with an itch measuring system (product of Neuroscience; when the mouse makes an action, the magnets move accordingly and a current flows through the coil; the moving magnets cause a change in the current, which is detected, measured and analyzed). Among the scratching actions, those lasting 1.5 seconds or longer were considered itch-evoked and their number was counted continuously. Since the itch-evoked scratching behavior had a diurnal rhythm, the diurnal rhythm of each individual animal was measured for 24 hours of the day before test and only after that, each of the test drugs dissolved in 100% ethanol was applied to the dorsal skin in a dose of 0.2 ml/mouse. The subsequent 24-hr itch-evoked scratching behavior was measured and the number of itch-evoked scratchings after drug administration was compared with the initial count. The experimental data was processed to calculate the percent itch suppression on the basis of the total 24-hr itch-evoked scratching counts before and after drug application. For significance testing, the itch-evoked scratching counts that were obtained before and after drug application from individual animals in each group treated with a specific concentration of drug were processed by a paired t-test.

Percent itch suppression (%)=(itch-evoked scratching count before drug application−itch-evoked scratching count after drug application)×100/itch-evoked scratching count before drug application (Results)

The structures of the compounds used in the test are shown below and the test results are shown in Table 5.

TABLE 5

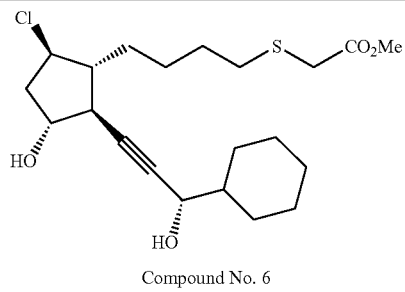

Compound No. 6

TABLE 5-continued

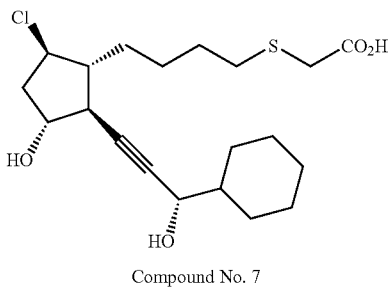

Compound No. 7

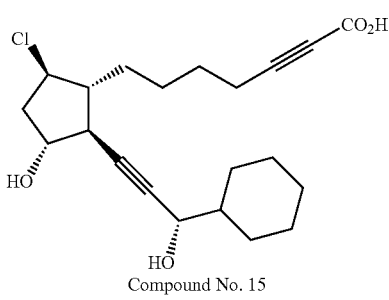

Compound No. 15

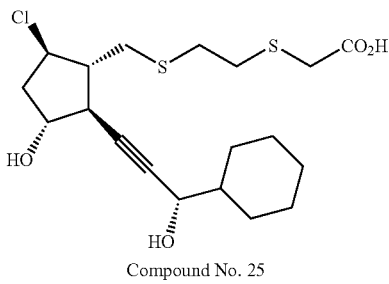

Compound No. 25

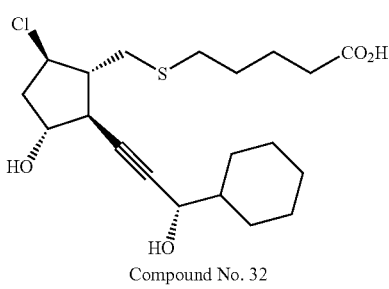

Compound No. 32

| Compound | Concentration (%) | Inhibition rate (%) | Efficacy |
|---|---|---|---|
| EtOH | 100 | 10.2 | NS |
| 6 | 0.0001 | 32.26 | * |
| 7 | 0.000001 | 43.26 | ** |
| 15 | 0.000001 | 34.61 | * |
| 25 | 0.00001 | 21.51 | * |
| 32 | 0.00001 | 41.76 | ** |

*$P < 0.05$,
**$P < 0.01$

Test Example 2

Effect on Dermatitis Manifesting NC Mouse Models

By suitably modifying a method known to the skilled artisan (Jpn. J. Pharmacol. 76, 175-183 (1998) Jun Hiroi, et al. Effects of Tacrolimus Hydrate (FK-506) Ointment on Spontaneous Dermatitis in NC/Nga Mice), the following test was conducted in order to confirm the antipruritic effect of compounds of the invention.

(Method)

Animals: Four-week old SPF NC mice (male) were purchased from Japan SLC; right after their arrival, the SPF NC mice were kept together with dermatitis manifesting male NC mice (older than 20 weeks) for 2 weeks under the following conditions so as to induce itch-evoked scratching behavior. A group of mice manifesting dermatitis and another group of mice not manifesting dermatitis, each consisting of four animals, were allowed to cohabit in a sawdust cage (34×17×39 cm) and kept in an animal house set at room temperature (23±3° C.) and at a humidity of 55±15% under illumination for 12 hours (from 7:00 am to 7:00 pm).

After 2-wk cohabitation, the purchased mice were taken out of the cage and transferred into another cage, where a group of 8 animals were kept for about 14 weeks. Immediately before the application of a drug, the mice were reshuffled so that the dermatitis scores would be equal among all cages and then kept, four animals per cage.

Tacrolimus was purchased from Fujisawa Pharmaceutical Co., Ltd. for use in the experiment.

Drug administration: To the dorsal backs of the 20-wk NC mice that were induced to manifest dermatitis as the result of cohabitation with the spontaneous dermatitis manifesting NC mice, 100% ethanol, compound No. 7 (0.01%) dissolved in 100% ethanol or tacrolimus (0.1%) dissolved in 100% ethanol was applied from an Eppendorf pipette in 200-µl doses seven times a week for a period of 4 weeks. The non-treatment group was not given any treatment. Each test group consisted of 8 animals that were observed for any dermatitic symptoms.

Dermatitis score: Dermatitic symptoms were observed and measured once a week.

Four factors, smoothness of fur, loss of hair, bleeding and scab formation, were rated by the following scores: 0, no symptom; 1, mild symptom; 2, moderate symptom; 3, severe symptom (minimum sum, 0; maximum sum, 12).

(Results)

The results of observation of dermatitic symptoms are shown in FIG. 1.

The groups administered with tacrolimus and compound No. 7 showed significant dermatitis score suppressing action compared to the vehicle group.

Test Example 3

Effect on the Spontaneous, Itch-Evoked Scratching Behavior of NC Mice

Experimental

Figure 2:
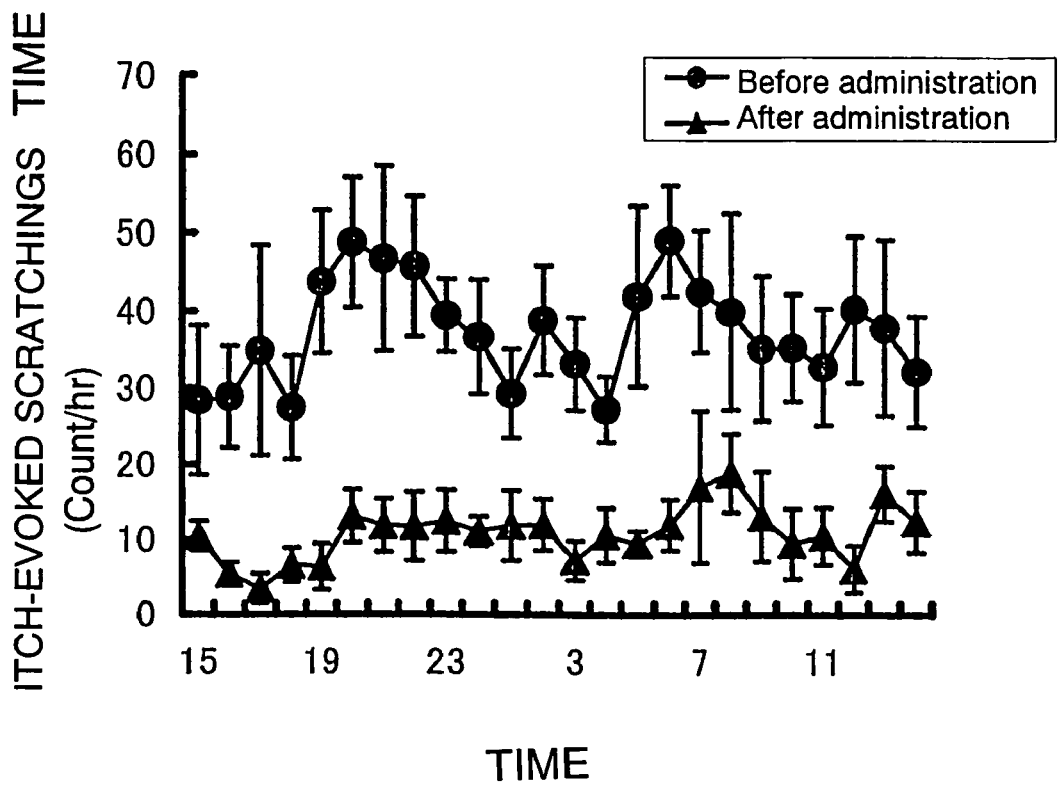
FIG. 2 shows the results of a test for suppressing spontaneous itch-evoked scratching behavior by administering compound No. 3.
Figure 2:
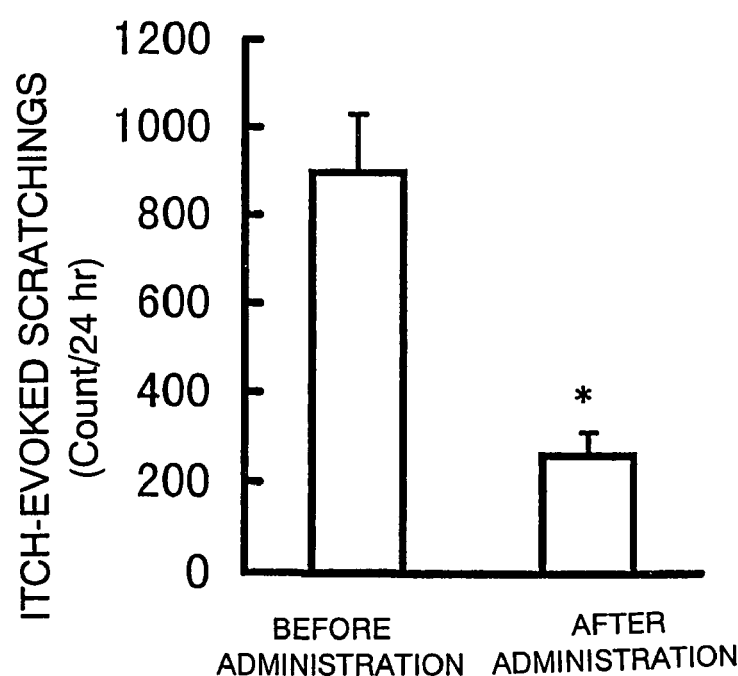
Figure 3:
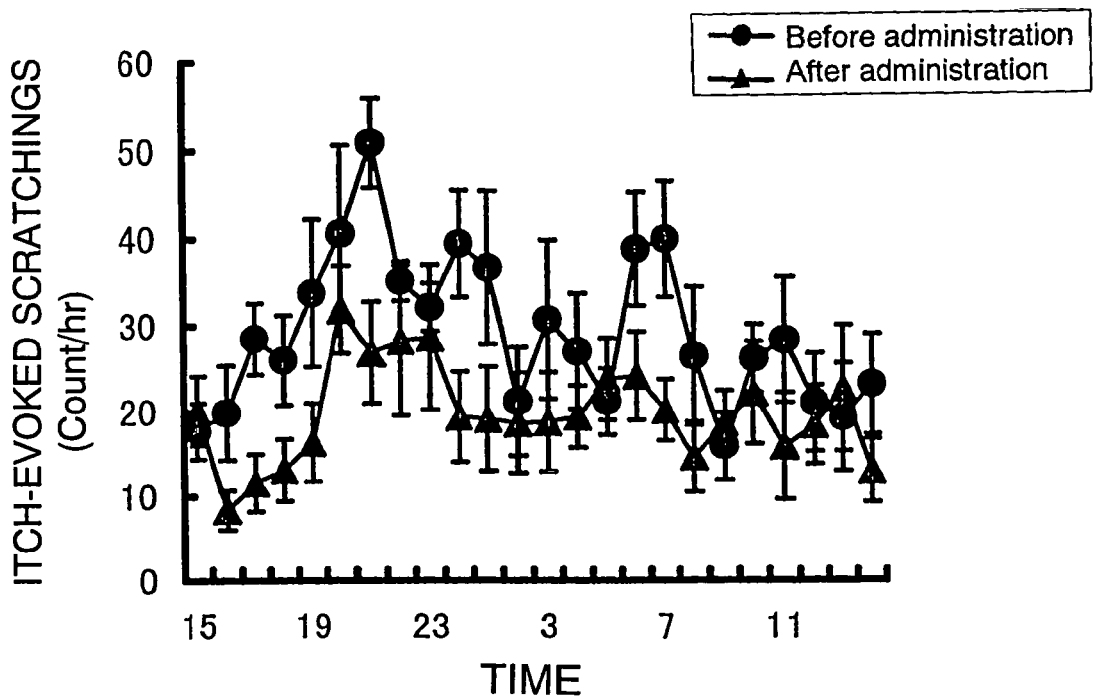
FIG. 3 shows the results of a test for suppressing spontaneous itch-evoked scratching behavior by administering compound No. 11.
Figure 3:
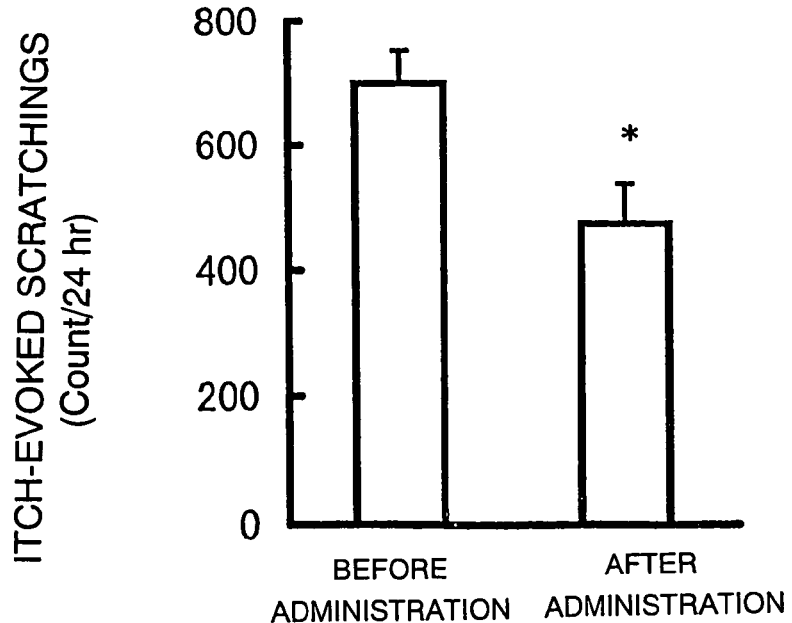
Figure 4:
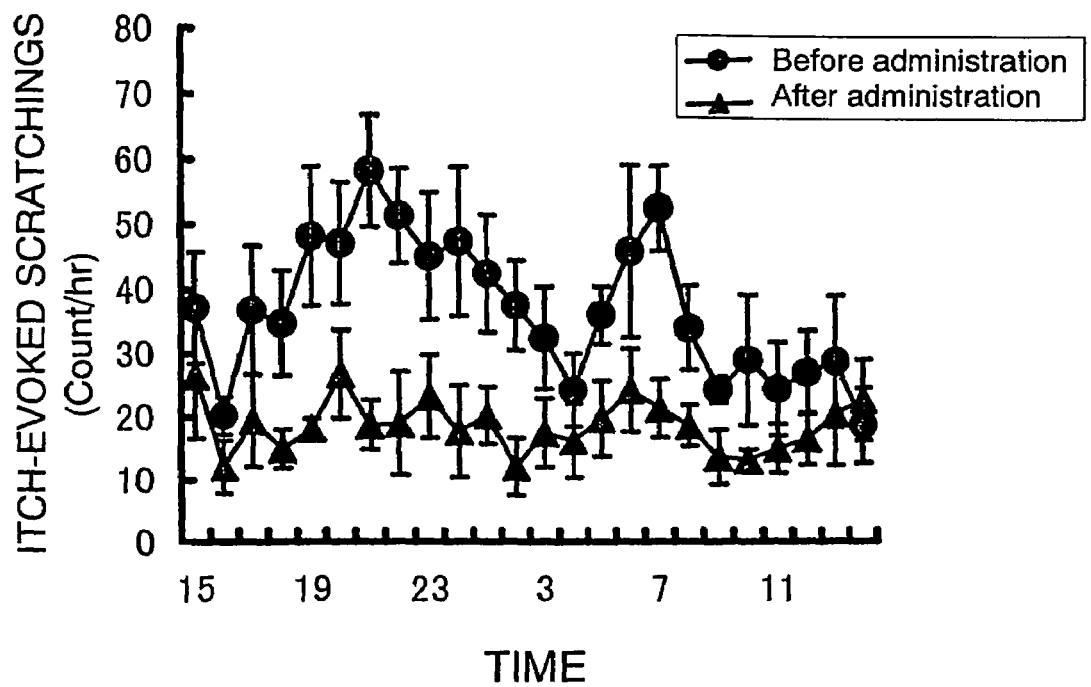
FIG. 4 shows the results of a test for suppressing spontaneous itch-evoked scratching behavior by administering compound No. 12.

About 20-week old NC/Nga mice each weighing about 30 g and manifesting atopic dermatitis were purchased from SLC and subjected to the following experiment. A magnet was buried in both hind paws of each mouse and by detecting its magnetism, the movement of the paws was measured with an itch measuring system (product of Neuroscience). Among the scratching actions, those lasting 1.5 seconds or longer were considered itch-evoked and their number was counted continuously. Since the itch-evoked scratching behavior had a diurnal rhythm, the diurnal rhythm of each individual animal was measured for 24 hours of the day before test and only after that, compound No. 3 (0.1%), compound No. 11 (0.1%)

or compound No. 12 (0.1%) dissolved in 100% ethanol was applied to the dorsal skin in a dose of 0.2 ml/mouse. The subsequent 24-hr itch-evoked scratching behavior was measured and the number of itch-evoked scratchings after drug administration was compared with the initial count. The structures of the test compounds are shown below and the changes with time in the spontaneous itch-evoked scratching counts, as well as the 24-hr total spontaneous itch-evoked scratching counts before and after administration of a compound are shown in FIGS. 2-4.

For significance testing, the itch-evoked scratching counts that were obtained before and after drug application from individual animals in each group treated with a specific concentration of drug were processed by a paired t-test.

Compound No. 3

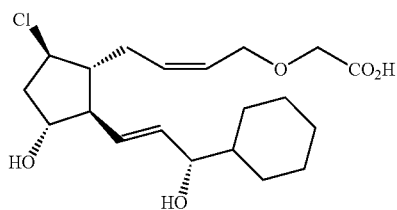

Compound No. 11

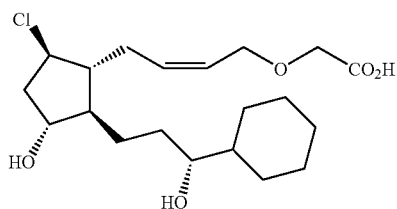

Compound No. 12

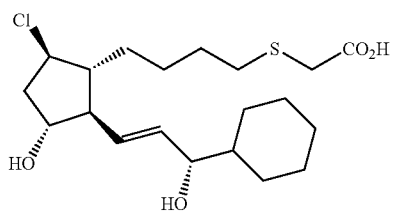

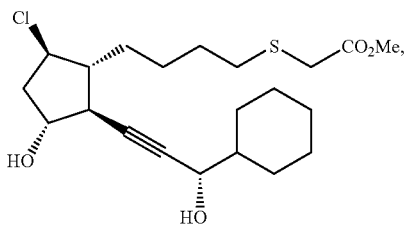

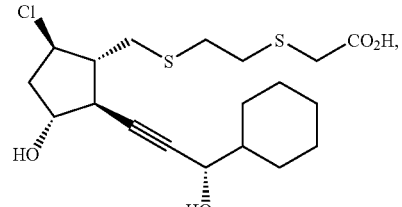

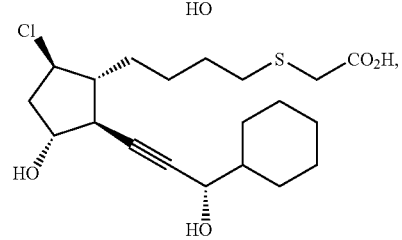

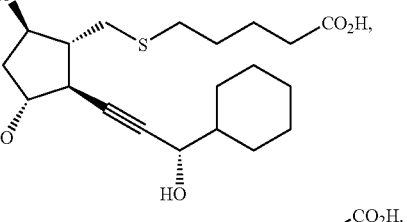

and

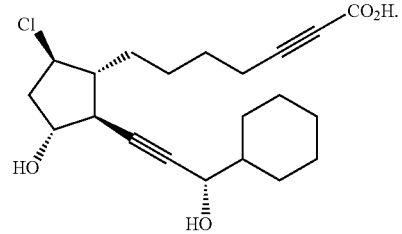

INDUSTRIAL APPLICABILITY

Having enabled reducing the frequency of itch-evoked scratching behavior that induces dermatitis, this invention successfully provides pharmaceutical preparations that can prevent or ameliorate various cases of dermatitis including atopic dermatitis, atopic conjunctivitis, scabies, urticaria and xerosis.

The invention claimed is:

1. A method of treating atopy-evoked pruritic symptoms which comprises administering to a mammal a therapeutically effective amount of a prostaglandin derivative represented by any of the following formulae, a pharmaceutically acceptable salt thereof or a hydrate thereof:

2. The method according to claim 1, wherein the atopy-evoked pruritic symptoms are those in atopic dermatitis or atopic conjunctivitis.

3. The method according to any one of claims 1 and 2 wherein the prostaglandin derivative is represented by the following formula, a pharmaceutically acceptable salt thereof or a hydrate thereof:

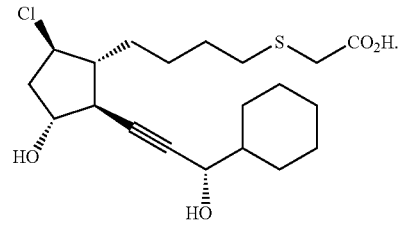

4. The method according to any one of claims 1 and 2 wherein the administering is achieved by external application.

* * * * *